United States Patent [19]

Narayanan

[11] Patent Number: 5,298,529
[45] Date of Patent: Mar. 29, 1994

[54] METHOD OF STABILIZING AQUEOUS MICROEMULSIONS USING A SURFACE ACTIVE HYDROPHOBIC ACID AS A BUFFERING AGENT

[75] Inventor: Kolazi S. Narayanan, Palisades Park, N.J.

[73] Assignee: ISP Investments Inc., Wilmington, Del.

[21] Appl. No.: 978,599

[22] Filed: Nov. 19, 1992

Related U.S. Application Data

[63] Continuation-in-part of Ser. No. 777,033, Oct. 16, 1991, abandoned, which is a continuation-in-part of Ser. No. 654,250, Feb. 12, 1991, abandoned, which is a continuation-in-part of Ser. No. 546,014, Jun. 28, 1990, Pat. No. 5,156,666, which is a continuation-in-part of Ser. No. 505,030, Apr. 5, 1990, Pat. No. 5,160,528, which is a continuation-in-part of Ser. No. 448,707, Dec. 11, 1989, Pat. No. 5,071,463.

[51] Int. Cl.$^5$ .............................................. A01N 25/00
[52] U.S. Cl. .................................... 514/788; 514/937; 514/970
[58] Field of Search ............... 514/970, 971, 937, 938, 514/788; 504/116

[56] References Cited

U.S. PATENT DOCUMENTS 4,840,663 6/1989 Quadranti et al. ................... 504/116

FOREIGN PATENT DOCUMENTS 0695393 7/1969 South Africa .

OTHER PUBLICATIONS

Chemical Abstracts (109:131269m) 1988.

*Primary Examiner*—Frederick E. Waddell
*Assistant Examiner*—K. Weddington
*Attorney, Agent, or Firm*—Marilyn J. Maue; Joshua J. Ward; Walter Katz

[57] ABSTRACT

A method of stabilizing aqueous microemulsions against hydrolysis or phase separation of the active ingredient therein comprising buffer the microemulsion to acidic conditions using a surface active hydrophobic acid having a pKa of about 2-5, which have a hydrophobic group capable of entering micelles to preclude an undesired increase in electrolyte strength in the bulk aqueous medium. The method is particularly applicable to active ingredients which ordinarily hydrolyze under basic conditions, or precipitate in an acid medium buffered by conventional inorganic acids. An embodiment of the invention comprises an aqueous microemulsion of a carbamate ester which is stabilized against hydrolysis or precipitation at a pH of about 6.5 with a buffer of nonylphenyl ethoxylated phosphoric acid.

19 Claims, No Drawings

METHOD OF STABILIZING AQUEOUS MICROEMULSIONS USING A SURFACE ACTIVE HYDROPHOBIC ACID AS A BUFFERING AGENT

CROSS-REFERENCE TO RELATED U.S. PATENT APPLICATIONS

This application is a continuation-in-part of application Ser. No. 777,033, filed Oct. 16, 1991, now abandoned which is a continuation-in-part of Ser. No. 654,250, filed Feb. 12, 1991,now abandoned which, in turn, is a continuation-in-part of application Ser. No. 546,014, filed Jun. 28, 1990, now U.S. Pat. No. 5,156,666 which, in turn, is a continuation-in-part of application Ser. No. 505,030, filed Apr. 5, 1990, now U.S. Pat. No. 5,160,520 which, in turn, is a continuation-in-part of application Ser. No. 448,707, filed Dec. 11, 1989 (now U.S. Pat. No. 5,071,463).

BACKGROUND OF THE INVENTION

1. Field of the Invention

This invention relates to stabilized aqueous microemulsions, and, more particularly, to a method of chemically and physically stabilizing aqueous microemulsions containing a water-insoluble active ingredient which normally is subject to hydrolysis under basic conditions, or phase separation in a conventionally buffered acid medium.

2. Description of the Prior Art

Microemulsions are oil-in-water or water-in-oil, clear, thermodynamically stable dispersions of two or more immiscible liquids wherein the dispersed phase consists of small droplets or micelles with diameters in the range of about 10 to 100 millimicrons. Aqueous microemulsion compositions are used to conveniently disperse active ingredients such as agriculturally active chemicals which are substantially insoluble in water. However, often aqueous microemulsions are observed to be unstable hydrolysis of the active ingredient and/or leakage of the active ingredient resulting in precipitation or crystallization in the water phase. For example, carbamates, esters, amides, phosphate esters and thiophosphates esters such as hydramethylnon, Carbaryl, and the like, are known to hydrolyze in water under basic conditions.

Accordingly, it is an object of this invention to provide a chemically and physically stabilized aqueous microemulsion of an active ingredient subject to hydrolysis and/or precipitation.

Another object of this invention is to provide a method of stabilizing aqueous microemulsions against hydrolysis and/or precipitation of a water-insoluble, agriculturally active ingredient therein.

These and other objects and features of the invention will be made apparent from the following description thereof.

SUMMARY OF THE INVENTION

A method of stabilizing aqueous microemulsions against hydrolysis or phase separation of the active ingredient therein comprising buffer the microemulsion to acidic conditions using a surface active hydrophobic acid having a pKa of about 2–5, which have a hydrophobic group capable of entering micelles to preclude an undesired increase in electrolyte strength in the bulk aqueous medium. The method is particularly applicable to active ingredients which ordinarily hydrolyze under basic conditions, or precipitate in an acid medium buffered by conventional inorganic acids. An embodiment of the invention comprises an aqueous microemulsion of a carbamate ester which is stabilized against hydrolysis or precipitation at a pH of about 6.5 with a buffer of nonylphenyl ethoxylated phosphoric acid.

DETAILED DESCRIPTION OF THE INVENTION

Many active ingredients, can be formulated as aqueous microemulsions, for example, agriculturally active chemicals, which are water-immiscible or oily liquids and/or solids. However, certain of these compounds, e.g. cyclo compounds, such as lactones, carbamates, and carbamate esters, animal and plant derivatives, synthetic pyrethroids, amides, diphenyl compounds, nonphosphates, organic phosphates, thiophosphates, and dithiophosphates normally exhibit chemical instability under basic conditions due to hydrolysis; or phase instability due to precipitation of the compound. Typical of such insecticides such as agriculturally active chemicals are carbamate esters, amides, phosphate esters, thiocarbamates, thiophosphate esters or esters of thiophosphates. These insecticide compounds include Carbaryl, Aminocarb, Alphacypermethrin, Resmethrin, Allethrin, Diflubenzuron, Dicrotophos, Profenofos, Azinphos-methyl, Methfuroxam, Procymidone, Fthalide, Nitrothal-isopropyl, Tolclofos-methyl, Pyrazophos, Chloropropham,EPTC,DPX-L5300, DPX-F 5384, and Naptalam. (A detailed description of each of these chemicals is set forth in Agricultural Chemical Books I, II, III, and IV, Insecticides, 1989; Herbicides (1986–1987); Fumigants and Growth Regulators (1988); Revision by W. T. Thomson, Thomson Publications.)

However, many of these compounds require a basic medium to form the aqueous microemulsion. For example, carbamate esters are formulated into aqueous microemulsions with anionic surfactants such as sodium dodecyl sulfate, and pesticides with ethanolamine. Such required basic conditions thus creates an unstable aqueous microemulsion.

What has been discovered herein is that these unstable microemulsions can be stabilized against hydrolysis and precipitation by buffering them with a hydrophobic acid having a pKa of about 2 to 5. These hydrophobic acids are surface active, i.e. their hydrophobic group or counter-ion can enter the micelles of the microemulsion while their hydrogen ion can be neutralized in the aqueous medium without increasing the electrolyte strength therein.

Suitable surface active hydrophobic acids for use herein include nonylphenyl ethoxylated phosphoric acid with an ethylene oxide unit content, i.e. —OCH$_2$CH$_2$ units (EO units) of from 3 to 18; R$_2$COOH where R$_2$ is C$_7$–C$_{17}$ alkyl, optionally with about 1 to 10 EO units;

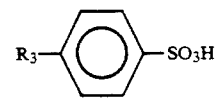

where R$_3$ is C$_8$–C$_{18}$ alkyl, optionally containing about 1 to 10 EO units; R$_4$SO$_3$H where R$_4$ is C$_8$–C$_{18}$ alkyl, optionally containing about 1 to 10 EO units; and R$_5$O-SO$_3$H where R$_5$ is C$_8$–C$_{18}$ alkyl, optionally containing about 1 to 10 EO units.

The amount of the surface active hydrophobic acid required to effect stabilization action usually is that amount necessary to buffer the aqueous microemulsion at a pH of about 4-6.5. A typical microemulsion concentrate for forming the aqueous microemulsion upon dilution comprises:

(a) about 1-25%, preferably 10-20%, by weight of an active ingredient (subject to hydrolysis under basic conditions), e.g. a carbamate ester;

(b) about 1-60%, preferably 5-50%, by weight of a surfactant, e.g. sodium dodecyl sulfate (SDS), e.g. an anionic surfactant; wherein the ratio of (a):(b) is 1:0.3 to 1:10, preferably 1:1 to 1:8, (c) about 15-90%, preferably 20-60%, by weight of a $C_1$-$C_4$ alkyl pyrrolidone, e.g. N-methyl pyrrolidone, or a $C_6$-$C_{18}$ alkyl pyrrolidone, e.g. N-octylpyrrolidone, or both;

(d) about 0.05-20%, preferably 0.1-10%, and most preferably about 0.2-1%, by weight of a surface active hydrophobic acid; and (e) 0-82.05% by weight of water.

Generally the typical microemulsion concentrate is diluted, usually with water, about 6-40,000, preferably 12-500 times, and more often 25-200 times, to form the aqueous microemulsion.

Surfactants suitable for use in the inventive composition include ethoxylated alkyl phenols, linear aliphatic polyesters, linear aromatic polyesters, polyalkenyloxyalcohol, linear aliphatic ethoxylates, polyethoxylated castor oil, polyethoxylated carboxylates, and polyethoxylated alkylamines. Anionic surfactants may be used as the emulsifier and include phosphate esters and their salts, alkyl sulfates, sulfonates, and their salts, salts of sulfated nonylphenoxypoly(ethyleneoxy) ethanol, salts of alkylbenzene sulfonates, salts of alkylnaphthalene sulfonate, and sulfonated aliphatic polyesters and their salts. Also suitable are complex phosphate esters of nonionic surfactants of the ethylene oxide type which are mixtures of diesters of phosphoric acid. (See, for example, McCutcheon's, *Emulsifiers and Detergents* (1989), published by McCutcheon's Division of M.C. Publishing Co., Glen Rock, N.J.).

Cosolvents include N-alkyl lactams for use in the invention are $C_1$-$C_4$ alkyl pyrrolidones, or $C_6$-$C_{18}$ alkyl pyrrolidones, or a mixture of both. A preferred $C_1$-$C_4$ alkyl pyrrolidone is N-methyl pyrrolidone; and a preferred $C_6$-$C_{18}$ alkyl pyrrolidone is N-octylpyrrolidone.

Experimental Procedure

A. Formulations

Formulations were prepared by weighing and mixing the exact proportions of the ingredients. Typically 100 g samples of the water-based formulations were prepared for each evaluation in 4 oz. stoppered bottles. When a lactam was used, the active ingredient was dissolved completely in the measured quantity of the lactam. The surfactant(s) was added to the active ingredient or to the solution of the active ingredient in the lactam (if a lactam was used). The contents were mixed in an automatic orbital shaker until the active ingredient dissolved completely or the mixture became homogeneous. Normally, this took about thirty minutes. A microemulsion concentrate was then obtained which was either diluted immediately or stored.

The water-based microemulsions were prepared by adding the required quantity of the concentrate to water. The dilution water was either deionized water or World Health Organization (WHO) standard hard water of hardness of 342 ppm expressed as $CaCO_3$ equivalent.

B. Evaluation of Stability

The samples were visually examined for clarity, precipitation, and separation or turbidity at ambient temperatures. Stable formulations were observed for as long as six months. The formulations were considered stable if they remained clear by visual observation for more than 4 days. Formulations that became cloudy or separated within 24 hours were considered unstable.

Promising formulations were evaluated for stability at lower and higher temperatures in the range from 10° C. through 45° C. Samples were stored at fixed temperatures of 10° C. through 45° C. and were observed visually as a function of time.

In a few cases, the clarity was also measured instrumentally and expressed as NTU (Nephelometric turbidity units) using a Hach Ratio Turbidimeter. Samples with values <50 NTU were considered visually clear.

Carbaryl is a well-known agriculturally active insecticide which is subject to hydrolysis under basic conditions. Accordingly, both the chemical and physical stability of aqueous microemulsions containing Carbaryl formulation below was determined under various conditions.

| AQUEOUS MICROEMULSION OF CARBARYL | |
|---|---|
| Carbaryl | 0.3 |
| SDS | 2 |
| N-octylpyrrolidone | 5 |
| Deionized Water | 92.7 |
| Results | |
| pH at time 0-1 hr. | 9.3 |
| Time, observation at ambient conditions: | |
| 0 time: | clear |
| 1 day: | clear |
| 4 days: | clear |
| 1 week: | clear, colorless |
| 2 weeks: | clear, colorless |
| 8 weeks: | clear, colored |
| 3 months: | clear, colored |
| 6 months: | colored, fine separation |

RESULTS

A. Control

The UV spectra at λ max=279 nm of solutions at 30 ppm active ingredient in ethanol prepared by appropriate dilution of the formulation (1/100) with ethanol was obtained as a function of time. The change in UV absorption was used to determine the decrease in Carbaryl concentration based on a calibration curve for the chemical. A 16% loss in activity was noticed in 40 days as determined by the UV spectra data, and still further deterioration thereafter. The pH of the formulation was alkaline throughout this period; however, it dropped from 9.3 to 7.4 at the 40 day period.

B. Buffer with $KH_2PO_4$

The formulation was buffered to a pH of 6 by the addition of $KH_2PO_4$. The thus-buffered formulation did not show any decay in the UV absorbance at λ max=279 nm of Carbaryl after a period of 30 days. However, tiny needles 150 μ in length started separating after 10 days.

C. Buffer with a Hydrophobic Acid

The formulation was buffered by adding a (~0.1 g to 100 g of formulation) of Gafac RE-610 (nonylphenyl ethoxylated phosphate ester) to bring the pH to 6. The resulting formulation showed no appreciable decay in the UV absorbance (no hydrolysis) or appearance of crystals (no precipitation) even after 120 days.

While the invention has been described with particular reference to certain embodiments thereof, it will be understood that changes and modifications may be made which are within the skill of the art. Accordingly, it is intended to be bound only by the following claims, in which:

What is claimed is:

1. A method of stabilizing an aqueous microemulsion containing a water-insoluble agriculturally active ingredient which aqueous microemulsion normally is chemically unstable due to hydrolysis under basic conditions and/or physically unstable due to precipitation of the active ingredient even when acid buffered with an inorganic acid comprising buffering the aqueous microemulsion to an acid condition with a hydrophobic acid which includes a surface active anion capable of entering the micelles of the microemulsion and a hydrogen ion to buffer the aqueous medium of the microemulsion to the desired acid condition without substantially increasing the ionic strength of the medium.

2. A chemically and physically stabilized aqueous microemulsion which is made by the method of claim 1.

3. A method according to claim 1 wherein said agriculturally active chemical is selected from a carbamate, an ester, an amide, a lactone or a carbamate ester.

4. A method according to claim 1 wherein said aqueous microemulsion is buffered with said hydrophobic acid to a pH of about 4–6.5.

5. A method according to claim 1 wherein said hydrophobic acid has a pKa of about 2 to 5.

6. A method according to claim 5 wherein said hydrophobic acid is selected from a nonylphenyl ethoxylated phosphoric acid with 3 to 18 EO units, $R_2COOH$ where $R_2$ is selected from $C_7$–$C_{17}$ alkyl and $C_7$–$C_{17}$ alkyl containing 1 to 10 EO units,

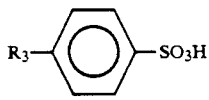

where $R_3$ is selected from $C_8$–$C_{18}$ alkyl and $C_8$–$C_{18}$ alkyl containing 1 to 10 EO units, $R_4SO_3H$ where $R_4$ is selected from $C_8$–$C_{18}$ alkyl and $C_8$–$C_{18}$ alkyl containing 1 to 10 EO units, and $R_5OSO_3H$ where $R_5$ is selected from $C_8$–$C_{18}$ alkyl and $C_8$–$C_{18}$ alkyl containing 1 to 10 EO units.

7. A microemulsion concentrate consisting essentially of:
   (a) about 1–25% by weight of an agriculturally active chemical,
   (b) about 1–60% by weight of an anionic surfactant, wherein the ratio of (a):(b) is 1:0.3 to 1:10,
   (c) about 15–90% by weight of an alkyl pyrrolidone selected from a $C_1$–$C_4$ alkyl pyrrolidone, and a $C_6$–$C_{18}$ alkyl pyrrolidone, and mixtures thereof, and
   (d) about 0.05 to 20% by weight of a surface active hydrophobic acid.

8. A method according to claim 1 wherein said stabilized aqueous microemulsion is prepared by diluting the microemulsion concentrate of claim 9 about 6–40,000 times with water to form an aqueous microemulsion containing at least 80% water.

9. A method according to claim 8 wherein said dilution factor is about 12–500.

10. A method according to claim 8 wherein said dilution factor is about 25–200.

11. A stabilized aqueous microemulsion made by the method of claim 8.

12. A microemulsion concentrate according to claim 7 wherein said ratio is 1:1 to 1:8.

13. A microemulsion concentrate according to claim 7 wherein said ratio is 1:2 to 1:5.

14. A microemulsion concentrate according to claim 7 wherein a mixture of said $C_1$–$C_4$ alkyl pyrrolidone and said $C_6$–$C_{18}$ alkyl pyrrolidone is present in the concentrate.

15. A microemulsion concentrate according to claim 7 wherein (a) is 4–20%, (b) is 5–50%, (c) is 20–60%, and (d) is 0.1–10%.

16. A microemulsion concentrate according to claim 7 wherein (d) is 0.1 to 10%.

17. A microemulsion concentrate consisting essentially of:
   (a) about 1–25% by weight of an agriculturally active ingredient,
   (b) about 1–75% by weight of a surfactant,
   (c) about 0–50% by weight of water, and
   (d) about 0.05–20% by weight of a surface active hydrophobic acid.

18. An aqueous microemulsion consisting essentially of the microemulsion concentrate of claim 17 diluted about 6–40,000 times with water.

19. An aqueous microemulsion according to claim 18 consisting essentially of 1 ppm–2% by weight of an agriculturally active ingredient, 1 ppm–6% by weight of a surfactant, 94–99.99% by weight of water, and 0.1 ppm–1% by weight of a surface active hydrophobic acid to buffer the microemulsion to a pH of about 4–6.5.

* * * * *